(12) United States Patent
Fontana et al.

(10) Patent No.: US 7,375,253 B2
(45) Date of Patent: *May 20, 2008

(54) PROCESS FOR THE PREPARATION OF (PER)FLUORINATED MONO-FUNCTIONAL CARBONYL COMPOUNDS

(75) Inventors: Giovanni Fontana, Verona (IT); Walter Navarrini, Milan (IT)

(73) Assignee: Solvay Solexis S.p.A., Milan (IT)

( * ) Notice: Subject to any disclaimer, the term of this patent is extended or adjusted under 35 U.S.C. 154(b) by 567 days.

This patent is subject to a terminal disclaimer.

(21) Appl. No.: 10/753,556

(22) Filed: Jan. 9, 2004

(65) Prior Publication Data

US 2004/0147778 A1 Jul. 29, 2004

(30) Foreign Application Priority Data

Jan. 9, 2003 (IT) .......................... MI2003A0019

(51) Int. Cl.
*C07C 43/00* (2006.01)
*C07C 51/58* (2006.01)
*C07C 53/38* (2006.01)

(52) U.S. Cl. .................. 568/615; 562/840; 562/849; 562/852; 562/856; 562/861

(58) Field of Classification Search ................ 568/615; 562/840, 849, 852, 856, 861, 862
See application file for complete search history.

(56) References Cited

U.S. PATENT DOCUMENTS

| | | | |
|---|---|---|---|
| 3,113,967 A | 12/1963 | Fawcett | |
| 3,175,378 A | 3/1965 | Russell | |
| 3,250,808 A | 5/1966 | Moore, Jr. | |
| 3,847,978 A | 11/1974 | Sianesi et al. | |
| 4,499,024 A | 2/1985 | Fifolt | |
| 4,827,024 A | 5/1989 | Guglielmo et al. | |
| 5,149,842 A | 9/1992 | Sianesi et al. | |
| 5,258,110 A | 11/1993 | Sianesi et al. | |
| 5,488,142 A | 1/1996 | Fall et al. | |
| 5,488,181 A | 1/1996 | Marchionni et al. | |
| 6,013,795 A | 1/2000 | Manzara et al. | |
| 6,127,498 A | 10/2000 | Tonelli et al. | |
| 2004/0147780 A1* | 7/2004 | Fontana et al. .............. | 562/852 |

FOREIGN PATENT DOCUMENTS

| | | |
|---|---|---|
| EP | 0 754 670 A2 | 1/1997 |
| GB | 1104482 | 4/1965 |
| GB | 1189337 | 7/1967 |

OTHER PUBLICATIONS

"A Simple Synthesis of Fluoroxyperfluoroalkyl Compounds," John K. Ruff et al., Communications to the Editor, Journal of the American Chemical Society, 88:19, Oct. 5, 1966, pp. 4531-4532.
"The Catalytic Addition of Fluorine to a Carbonyl Group. Preparation of Fluoroxy Compounds," Max Lustig et al., Journal of the American Chemical Society, 89:12, Jun. 7, 1967, pp. 2841-2843.
"Bis(fluoroxy)difluoromethane, $CF_2(OF)_2$," Frederick A. Hohorst et al., Journal of the American Chemical Society, 89:8, Apr. 12, 1967, pp. 1809-1810.
"Advances in the Chemistry of Organofluorine Hypohalites and Related Compounds," F.M. Mukhametshin, Russian Chemical Reviews, 49 (7), 1980, pp. 668-682.

* cited by examiner

*Primary Examiner*—Yvonne Eyler
*Assistant Examiner*—M Louisa Lao
(74) *Attorney, Agent, or Firm*—Arent Fox LLP.

(57) ABSTRACT

A process for the synthesis of (per)fluorinated mono-functional carbonyl compounds having the following formula (I):

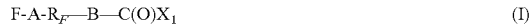

wherein:
$X_1 = F, CF_3$;
A, B equal to or different from each other, are independently (per)fluoroalkylene or (per)fluorooxyalkylene groups;
$R_F$ is $-ORf_1O-$ wherein $Rf_1$=perfluoroalkylene or $-ORf_2$, wherein $Rf_2$ is a perfluorooxyalkylene chain;
said process comprising the following steps:
A) obtainment of the formula (II) mono-hypofluorite:

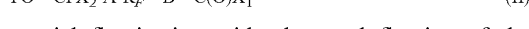

by partial fluorination with elemental fluorine of the carbonyl groups of the formula (III) compound:

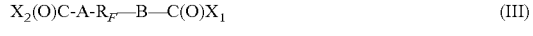

in the presence of a formula MeFy catalyst, Me being an alkaline or alkaline-earth metal or Ag, y=1 or 2;
B) thermal decomposition of the compound (II) to give the compounds according to the following scheme:

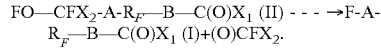

21 Claims, No Drawings

PROCESS FOR THE PREPARATION OF (PER)FLUORINATED MONO-FUNCTIONAL CARBONYL COMPOUNDS

The present invention relates to a process for preparing (per)fluorinated mono-functional carbonyl compounds starting from (per)-fluorinated di-functional carbonyl compounds.

Various preparation methods for obtaining mono-functional carbonyl (per)fluorinated compounds are known.

U.S. Pat. No. 3,113,967 describes the synthesis of perfluoro-mono-acyl-fluorides by condensation of $COF_2$ with perfluoroolefins. In the reaction, as catalysts, salts capable to make available the ion fluoride are used and optionally dipolar aprotic solvents can be used. This process has the drawback to be limited by the need to have available cheap fluoroolefins. Besides, the Examples show that high yields are obtained only when one operates in the presence of a solvent.

U.S. Pat. No. 3,250,808 describes perfluoromonoacylfluorides of formula $Rf_2O[CF(CF_3)CF_2O]_{nI}CF(CF_3)C(O)F$ wherein nI=0-100, and the process for their preparation. The synthesis has the drawback to use perfluoropropene epoxide (HFPO), which must be previously prepared by controlled perfluoropropene oxidation. A further drawback is that a dipolar aprotic solvent must be used at the anhydrous state.

U.S. Pat. No. 6,013,795 describes a new class of fluoroalkylcarbonyl compounds alpha branched to carbonyl. Said compounds, preferably having at least 8 carbon atoms, are synthesized starting from the corresponding hydrogenated precursors according to the classic fluorination methods with $F_2$, or the electrochemical route with HF. The drawback of this process is that in the fluorination high amounts of fluorine per mole of synthesized perfluoroacylfluoride must be used. Besides, in some cases, for example when oxygen atoms are present in the starting compound, the hydrofluoric acid formed during the fluorination causes the decompostion of the molecule to be fluorinated.

U.S. Pat. No. 3,847,978 describes the preparation of perfluoropolyether acylfluorides of formula $AO(C_3F_6O)_{mIV}(C_2F_4O)_{lIV}(CF_2O)_{nIV}$—B, wherein A and B equal to or different from each other can be: —$CF_3$, —C(O)F, —$CF_2$C(O)F, —$CF(CF_3)C(O)F$, —$CF_2C(O)CF_3$. The process requires the reduction of a peroxidic linear perfluoropolyether polymer of formula: $A-O(C_3F_6O)_{mIV}(C_2F_4O)_{lIV}(CF_2O)_{nIV}(O)_{sIV}$—B, wherein A and B have the above meaning. The Examples show that the process has a high selectivity for obtaining perfluoropolyether diacylfluorides (acylfluoride groups in both end groups A and B), while the selectivity is poor for the mono-functional acylfluoride derivatives.

EP 754,670 describes mono-hypofluorite compounds of formula $FC(O)$—$Rf_{III}$—$CF_2OF$, wherein $Rf_{III}$ is a $C_1$-$C_{12}$ perfluoroalkylene or perfluorooxyalkylene chain having a molecular weight in the range 100-2,000, and the process for the preparation thereof. The process requires the hypofluorite synthesis in liquid phase, in the presence of a catalyst, by fluorination of diacylfluorides at temperatures in the range from −40° C. to +40° C. The used catalysts are the salts of general formula $MeF_{yV} \cdot zvHF$, wherein Me is an alkaline or alkaline-earth metal, for example $KHF_2$ or $CsHF_2$. In the patent it is shown that by using an alkaline or alkaline-earth metal fluoride catalyst of formula $MeF_{yV}$, only bis-hypofluorites are obtained. In particular in the comparative Examples it is shown that by using in the reaction CsF or KF, by operating at the temperature of −10° C., a mixture formed of bis hypofluorites and starting reactants is obtained.

The need was felt to have available a synthesis of (per)fluorinated mono-functional carbonyl compounds working even in the absence of solvent, also in a semicontinuous and continuous way, having good yields in mono-functional carbonyl (per)fluorinated compounds.

The Applicant has surprisingly and unexpectedly found a synthesis process of mono-functional carbonyl (per)fluorinated compounds able to solve the above technical problem.

It is an object of the present invention a process for the synthesis of (per)fluorinated mono-functional carbonyl compounds having the following formula:

$$F\text{-}A\text{-}R_F\text{—}B\text{—}C(O)X_1 \quad (I)$$

wherein:

$X_1$=F, $CF_3$;

A, B equal to or different from each other, can independently be $C_1$-$C_5$ (per)fluoroalkylene groups or linear or branched $C_1$-$C_5$ (per)fluorooxyalkylene groups, optionally containing one or more Cl and/or H atoms;

$R_F$ is selected from the following groups:

—$ORf_1O$— wherein $Rf_1$=$C_1$-$C_{20}$ perfluoroalkylene;

—$ORf_2$-, wherein $Rf_2$ is a perfluorooxyalkylene chain containing one or more of the following units statistically distributed along the backbone:

($C_3F_6O$), selected between ($CF_2CF(CF_3)O$) or ($CF(CF_3)CF_2O$);

($CFX_1O$) wherein $X_1$ is F or $CF_3$;

($C_2F_4O$);

($CF_2(CF_2)_{x'}CF_2O$) wherein x' is an integer equal to 1 or 2;

($CR_4R_5CF_2CF_2O$) wherein $R_4$ and $R_5$ are equal to or different from each other and selected between H, Cl, and wherein one fluorine atom of the perfluoromethylene unit can be optionally substitued with H, Cl or (per)fluoroalkyl, having for example from 1 to 4 carbon atoms;

said process comprising the following steps:

A) obtainment of the mono-hypofluorite of formula:

$$FO\text{—}CFX_2\text{-}A\text{-}R_F\text{—}B\text{—}C(O)X_1 \quad (II)$$

by fluorination with elemental fluorine of the carbonyl groups of the following (per)fluorinated di-functional carbonyl compound of formula:

$$X_2(O)C\text{-}A\text{-}R_F\text{—}B\text{—}C(O)X_1 \quad (III)$$

wherein:

$X_1$, $R_F$, A and B have the above meanings;

$X_2$, equal to or different from $X_1$, has the same meanings as $X_1$;

in the presence of a catalyst based on metal fluorides having formula MeFy, wherein:

Me is an alkaline or alkaline-earth metal or Ag;

y=1 or 2;

B) thermal decomposition of the mono-hypofluorite of formula (II) to give (per)fluorinated mono-functional carbonyl compounds (I), according to the reaction:

$$FO\text{—}CFX_2\text{-}A\text{-}R_F\text{—}B\text{—}C(O)X_1 \text{ (II)} \dashrightarrow F\text{-}A\text{-}R_F\text{—}B\text{—}C(O)X_1 \text{ (I)} + (O)CFX_2.$$

The preferred A and B groups in the formulas (I)-(III) are selected from the following:

—$CF_2$—, —$CF(CF_3)$—, —$CF_2CF_2$—, —$CF_2CF_2CF_2$—, —$CF_2CF(CF_3)$—, —$CF(CF_3)CF_2$—, —$CF(OCF_3)$—, —$C(OCF_3)_2$—, —$C(CF_3)(OCF_3)$—.

Preferably, when $R_F$=—$ORf_2$-, the perfluorooxyalkylene chain $Rf_2$ is selected from the following:

a') —$(CF_2CF_2O)_m(CF_2O)_n(CF_2CF(CF_3)O)_p(CF(CF_3)O)_q(CF_2CF_2O)_r$—,
b') —$(CF_2O)_n(CF_2CF(CF_3)O)_p(CF(CF_3)O)_q$—,
c') —$(CF_2CF_2O)_m(CF_2O)_n$—, wherein:
  m is comprised between 0 and 100, extremes included,
  n is comprised between 0 and 100, extremes included,
  p is comprised between 0 and 60, extremes included,
  q is comprised between 0 and 60, extremes included,
  r is comprised between 0 and 60, extremes included, m+n+p+q+r being ≧0 and the number average molecular weight of —$ORf_2$— in the range 16-12,000, preferably 16-5,000, still more preferably 60-3,000.

In particular in the formula c') m and n, independently the one from the other, have the above values and, preferably, when m and n are both present, are such whereby m/n ranges from 0.2 to 12 with a number average molecular weight of —$ORf_2$— within the above values.

Step A), fluorination of the di-functional carbonyl compounds (III), can be carried out in the presence or in the absence of solvents, inert under the reaction conditions. In step A) the molar ratio $F_2$/carbonyl groups of compound (III) generally ranges from 0.05 to 0.90, preferably from 0.1 to 0.80; the reaction temperature ranges from −80° C. to +30° C.

Preferably in step A) one operates in the absence of solvents.

In step A) preferably the catalysts based on metal fluorides are selected from the following:
  alkaline or alkaline-earth metal fluorides selected from the following: CsF, KF, RbF, LiF, NaF, $CaF_2$, $BaF_2$, $MgF_2$, $SrF_2$;
  AgF;

said catalysts can be used as such, or mixed with each other or optionally supported on porous material.

As porous support material, it can be used the porous materials available on the market and inert under the reaction conditions. $AlF_3$ can for example be mentioned.

The preferred metal fluorides are CsF and KF.

The catalyst can be used for long periods in the process according to the present invention, without the need to be regenerated.

The fluorination reaction can be carried out at a pressure equal to or higher than the atmospheric pressure, for example up to 5 atmospheres.

When in the fluorination reaction solvents are used, they are selected for example among the following: $C_3F_8$, $C_4F_8$ (cycle) $C_3F_8O$(ether), $C_4F_{10}O$(ether), $CF_3O(CF_2)_2$—$CF_3$, $CF_4$, $C_2F_6$, perfluoropolyethers.

Furthermore it has been surprisingly found that the fluorination reaction selectivity of (per)fluorinated di-functional carbonyl compounds to give (per)fluorinated mono-functional carbonyl compounds depends on the used catalyst and on the fluorination temperature. By using the same catalyst, the selectivity in monoacylfluoride (I), with respect to the converted diacylfluoride (III) increases with the temperature. See the Examples.

The hypofluorite thermal decomposition reaction B) is carried out subsequently to the fluorination reaction of the (per)fluorinated di-functional carbonyl compound.

The hypofluorite decomposition reaction temperature must be in the range between the temperature $T_i$, wherein the hypofluorite begins to decompose with formation of C(O)$FX_2$ as above defined, and $T_i+20°$ C., preferably $T_i+5°$ C.

The skilled man in the field is able to determine the $T_i$ temperature by slowly heating, for example with a gradient of 1° C./min., an hypofluorite (II) sample and detecting by IR spectroscopy the appearance of the peaks corresponding to the species C(O)$FX_2$ ($COF_2$, signals at 1928, 1944, 1956 $cm^{-1}$ and/or $CF_3COF$ signal at 1898 $cm^{-1}$), showing the hypofluorite decomposition. See the Examples.

The temperature at which the decomposition reaction is carried out is generally from 0° C. to +200° C., preferably from +40° C. to +150° C.

The invention process can be carried out in a discontinuous, semicontinuous and continuous way.

In the process according to the invention in step A), the fluorine conversion is generally higher than 90%.

The yield in perfluoroalkyl or perfluorooxyalkyl neutral end groups of formula (I) with respect to the converted carbonyl end groups, is higher than 90%, preferably higher than 95%.

The discontinuous and semicontinuous processes require the use of only one reactor, wherein the fluorination to obtain hypofluorite and the subsequent decomposition of the compound are carried out.

In the discontinuous process only one addition of fluorine to the suspension containing the catalyst, the (per)fluorinated di-functional carbonyl compound and the optional solvent respectively, is carried out.

After the fluorination, the reaction mixture is very slowly heated up to the complete decomposition of the hypofluorite to give neutral end groups.

In the semicontinuous process the gaseous fluorine, optionally diluted with a gas, inert under the reaction conditions, for example nitrogen and/or helium, is fed at the above temperatures in the suspension containing the catalyst and the formula (III) di-functional carbonyl compound. The fluorine is fed until obtaining the desired conversion percentage of the starting carbonyl end groups into hypofluorite end groups.

Preferably the fluorine is fed divided in aliquots, with respect to the needed total amount. After having fluxed the fluorine aliquot, the reaction mixture temperature is gradually increased to decompose the hypofluorite formed in the fluorination. At this point the reaction mixture temperature is lowered again to the initial value and one proceeds to a further fluorination. The cycle is repeated until obtaining the desired conversion percentage of the starting carbonyl end groups into neutral end groups. This percentage is in the range 5%-90%, preferably 10%-80%. The conversion percentage of the starting carbonyl end groups can, for example, be determined by $^{19}$FNMR.

In the semicontinuous process the fluorination of the (per)fluorinated di-functional carbonyl compound and the hypofluorite decomposition are carried out in an only one reactor.

At the end of the hypofluorite decomposition, the reaction product is separated from the catalyst and from the optional solvent by using known separation methods, as, for example, filtration, distillation or stripping under vacuum.

The continuous process requires the use of two separate reactors, the former for the fluorination of the (per)fluorinated di-functional carbonyl compound in the presence of the metal fluoride catalyst, the latter, working at a higher temperature, wherein the hypofluorite decomposition takes place.

In particular the fluorination reaction can be carried out by separately feeding on the catalyst gaseous fluorine, optionally diluted with an inert gas selected from those above mentioned and the di-functional carbonyl (per)fluorinated compound.

The hypofluorite, in admixture with the unreacted (per)fluorinated di-functional carbonyl compound, is fed from the fluorination reactor to the second reactor wherein the hypofluorite decomposition takes place.

In the continuous process, at the end of step B), the reaction mixture containing the unreacted di-functional carbonyl compounds, the mono-functional carbonyl compounds and those having both neutral end groups, is continuously taken from the bottom of the second reactor and re-fed to the first fluorination reactor. The cycle is repeated until obtaining the desired conversion percentage of the starting carbonyl end groups into neutral end groups. The conversion of the starting carbonyl end groups is within the limits indicated above for the semicontinuous process.

At the end the reaction mixture is collected in the second reactor and the products are separated and purified by distillation.

The continuous process shows the advantage to control and limit the hypofluorite concentration within very low and constant values. Besides it significantly facilitates the separation and final purification of the mono-functional carbonyl compound from the catalyst. This type of process is preferred when the catalyst is supported.

In the invention process it is preferred to operate in the absence of solvents.

With the invention processes one can operate even under such conditions that in the reaction mixture the (per)fluorinated di-functional carbonyl compounds of formula (III) are substantially absent, by using the minimum fluorine amount necessary to obtain the total conversion of the starting compound (III).

The total conversion of the starting compound is determined by GC/MS analysis, until disappearance of the starting compound. The fluorination reaction can be carried out also using an amount of fluorine higher than that above defined. However working in this way can bring to a yield reduction. The complete conversion of the perfluorinated di-functional carbonyl compounds of formula (III) in the reaction mixture is particularly useful from the industrial point of view since it allows an easy separation of the (per)fluorinated mono-functional carbonyl compounds of formula (I) from the reaction mixture; to separate the compound (I) it is preferable to transform it into its functional derivatives, for example acids esters or amides, preferably acids.

The starting (per)fluorinated di-functional carbonyl compounds of formula (III) can be prepared by synthesis of the peroxidic raw product and subsequent reduction. The peroxidic raw product synthesis is carried out by oxidative polymerization of fluoroolefins, in particular of $C_3F_6$ and/or $C_2F_4$, with oxygen at low temperature in the presence of UV light or of a radical initiator, such as described for example in patents GB 1,189,337, GB 1,104,482, U.S. Pat. Nos. 3,683,027, 3,175,378, 5,149,842, 5,258,110, 5,488,181.

The reduction of the peroxidic raw product is carried out with hydrogen on suitable catalyst containing palladium to give di-functional carbonyl perfluoropolyether compounds, for example as described in patents U.S. Pat. Nos. 3,847,978, 6,127,498. Furthermore the di-functional carbonyl compounds ar obtainable by direct fluorination, as described for example in U.S. Pat. No. 5,488,142.

The catalysts used in the present invention process are known in the art for the preparation of hypofluorites. U.S. Pat. Nos. 4,827,024, 4,499,024, EP 754,670; Ruff J. K. et al., J. Am. Chem Soc. 88:19 (1966), 4531-4532; Lustig et al., J. Am. Chem. Soc. 89:12 (1967), 2841-2843; Hohorst A. et al., J. am Chem Soc. 89:8 (1967), 1809-1810 can be mentioned.

The preferred di-functional carbonyl (per)fluorinated compounds of formula (III) to carry out the invention process are selected from the following:

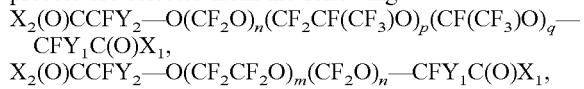
$X_2(O)CCFY_2$—$O(CF_2O)_n(CF_2CF(CF_3)O)_p(CF(CF_3)O)_q$—$CFY_1C(O)X_1$, $X_2(O)CCFY_2$—$O(CF_2CF_2O)_m(CF_2O)_n$—$CFY_1C(O)X_1$, wherein:
$X_1$, $X_2$, equal or different, are as above,
$Y_1$, $Y_2$, equal or different, have the $X_1$ meaning,
m, n, p, q are as above.

Still more preferred among the formula (III) compounds are the following:
$F(O)CCF_2O(CF_2O)_n$—$CF_2C(O)F$,
$F(O)CCF_2O(CF_2CF_2O)_m$—$CF_2C(O)F$,
$F(O)CCF_2O(CF_2CF_2O)_m(CF_2O)_n$—$CF_2C(O)F$, wherein m and n are as above defined.

Among the formula (III) compounds the following compounds are further preferred:
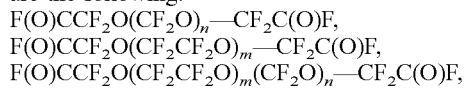
$F(O)CCF_2OCF_2C(O)F$, $F(O)CCF_2OCF_2OCF_2C(O)F$,
$F(O)CCF_2OCF_2CF_2OCF_2C(O)F$,
$F(O)CCF_2OCF_2OCF_2CF_2OCF_2C(O)F$, $F(O)CCF_2OCF_2OCF_2OCF_2C(O)F$,
$F(O)CCF_2OCF_2CF_2OCF_2CF_2OCF_2C(O)F$.

The mono-functional carbonyl (per)fluorinated compounds of formula (I) obtained by the invention process are preferably the following:

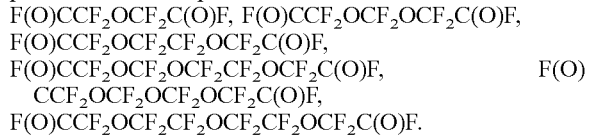
$CF_3$—$O(CF_2O)_n(CF_2CF(CF_3)O)_p(CF(CF_3)O)_q$—$CF_2C(O)F$,
$CF_3CF_2$—$O(CF_2O)_n(CF_2CF(CF_3)O)_p(CF(CF_3)O)_q$—$CF(CF_3)C(O)F$,
$CF_3CF_2$—$O(CF_2O)_n(CF_2CF(CF_3)O)_p(CF(CF_3)O)_q$—$CF_2CF_2C(O)F$,
$CF_3$—$O(CF_2CF_2O)_m(CF_2O)_n$—$CF_2C(O)F$,
$CF_3CF_2$—$O(CF_2CF_2O)_m(CF_2O)_n$—$CF(CF_3)C(O)F$,
$CF_3CF_2$—$O(CF_2CF_2O)_m(CF_2O)_n$—$CF_2CF_2C(O)F$, wherein m, n, p and q are as above.

The following formula (I) compounds are still more preferred:
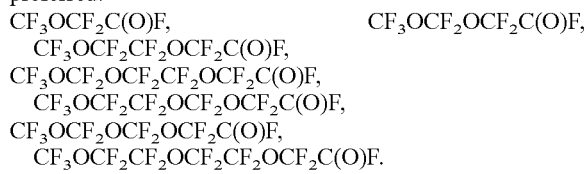
$CF_3OCF_2C(O)F$, $CF_3OCF_2OCF_2C(O)F$,
$CF_3OCF_2CF_2OCF_2C(O)F$,
$CF_3OCF_2OCF_2CF_2OCF_2C(O)F$,
$CF_3OCF_2CF_2OCF_2OCF_2C(O)F$,
$CF_3OCF_2OCF_2OCF_2C(O)F$,
$CF_3OCF_2CF_2OCF_2CF_2OCF_2C(O)F$.

It has been surprisingly found by the Applicant that it is possible to use the catalysts based on the above metal fluorides, for example CsF and KF, to obtain the formula (II) mono-hypofluorites, by fluorination of the (per)fluorinated di-functional carbonyl compounds of formula (III).

This is quite unexpected since according to the above discussed prior art said catalysts are not useful to obtain monohypofluorites (II) from (per)fluorinated di-functional carbonyl compounds (III).

Furthermore the Applicant has surprisingly found that in the invention process it is possible to decompose in a controlled way the monohypofluorite (II) to give (per)fluorinated mono-functional carbonyl compounds (I), substantially avoiding the formation of undesired by-products.

This is unexpected since there is no teaching in the prior art relating to this specific feature of the monohypofluorite decomposition process. Indeed it is known that hypofluorites, owing to the low power of the —OF bond, tend to decompose with highly exothermal reactions forming various by-products. See for example in Russian Chemical Reviews 49 (7) 1980, 668-682.

The perfluorinated mono-functional carbonyl compounds are useful compounds in the chemical industry. The perfluorinated mono-acyl fluorides can be transformed into other functional groups as acids, salts, esters, amides, ethers. Said derivatives are usefully employed as surfactants or additives, or as intermediates for the synthesis of various fluorinated derivatives.

Furthermore monoacylfluorides are useful compounds for the preparation of perfluorovinylethers by the fluorination into the corresponding hypofluorites and subsequent sum to (per)fluoroolefins, for example CFCl=CFCl. Said monomers are used in the synthesis of fluoroelastomers and fluoroplastomers.

Besides, the mono-acyl fluorides are used for the preparation of perfluorodiacyl-peroxides, polymerization initiators useful for obtaining fluoropolymers having perfluorinated end groups.

The following non limitative Examples illustrate the invention.

EXAMPLES

Example 1

Syntesis in a Discontinuous Way of Monoacylfluoride $CF_3O—(CF_2CF_2O)_m(CF_2O)_n—CF_2C(O)F$ by Fluorination of the corresponding diacylfluorides on CsF catalyst at the temperature of $-10°$ C. and subsequent decomposition in situ of the obtained hypofluorites.

In a 10 cc metal reactor equipped with internal thermocouple there are introduced 0.9 g of CsF catalyst (Aldrich®, titre 99.9%), which is dried by heating under vacuum at 200° C. for two hours and successively fluorinated at 400 mbar ($4×10^4$ Pa) of fluorine at the temperature of 150° C. for 2 hours. After elimination of the residual fluorine, 2 mmoles of diacylfluorides are introduced, having formula:

$$F(O)CCF_2O—(CF_2CF_2O)_m(CF_2O)_n—CF_2C(O)F \qquad (IIIA),$$

number average MW (MN) 620, m/n ratio=4.30 and functionality in —COF end groups of 1.82 and functionality in —$CF_2CF_3$ end groups of 0.18, determined by NMR. The diacylfluoride has been prepared as described in patents U.S. Pat. Nos. 5,258,110 and 3,847,978.

After cooling in liquid nitrogen ($-196°$ C.), the optional uncondensable products ($N_2$, $O_2$) stripped, 1.82 mmoles of fluorine are added and the reaction mixture is brought to $-10°$ C. and maintained at this temperature for 4 hours. It is cooled to $-196°$ C. and it is noticed that the fluorine conversion is complete. The reaction mixture is then let increase up to $-10°$ C. without variation of the internal pressure, which indicates that the hypofluorites formed under said conditions are stable. Then the temperature is slowly increased, with a gradient of 1° C./min. under temperature and internal pressure control. At the temperature of about 40° C. it is noticed the decomposition of the obtained hypofluorites with exothermal reaction and $COF_2$ formation, as detected by IR analysis of the gaseous phase. After the reaction mixture has been brought to 50° C. for 1 hour to complete the hypofluoprite decomposition, it is cooled to $-50°$ C. and the $COF_2$ produced in the reaction is removed by water pump.

The reaction products are then recovered in $C_6F_6$ and analyzed by $^{19}F$—NMR analysis. The conversion of initial —COF end groups to quantitatively give —$OCF_3$ groups is 47%; the fed fluorine yield is 94%.

The GC/MS and GC analyses show that the following reaction compounds a) (monoacylfluoride) and b) (neutral perfluoropolyether) form beside the starting unreacted diacylfluorides c) with the following relative molar percentages, determined by gaschromatography:

| | | |
|---|---|---|
| a) | $CF_3O—(CF_2CF_2O)_m(CF_2O)_n—CF_2C(O)F$ | 19% |
| b) | $CF_3O—(CF_2CF_2O)_m(CF_2O)_n—CF_3$ | 42% |
| c) | $F(O)CCF_2O—(CF_2CF_2O)_m(CF_2O)_n—CF_2C(O)F$ | 39% |

The reaction compounds a) and b) were obtained respectively by the synthesis of the corresponding mono-hypofluorites (1) and bis-hypofluorites (2) reported hereinunder:

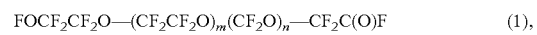
$$FOCF_2CF_2O—(CF_2CF_2O)_m(CF_2O)_n—CF_2C(O)F \qquad (1),$$

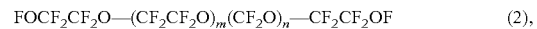
$$FOCF_2CF_2O—(CF_2CF_2O)_m(CF_2O)_n—CF_2CF_2OF \qquad (2),$$

by fluorination of the initial diacylfluorides (IIIA) and subsequent degradation of the obtained hypofluorites (1) and (2), as the temperature increases, as above indicated.

The yield of the monoacylfluorides a) calculated with respect to the initial converted diacylfluorides is 31%.

The reaction products are separated by fractional distillation.

Characterization of the Products: $^{19}F$—NMR $^{19}F$—NMR spectrum in p.p.m. with respect to $CFCl_3$ (p.p.m.=0): 13.2 (1F $\underline{F}(O)CCF_2OCF_2O$—); 13.0 (1F $\underline{F}(O)CCF_2OCF_2CF_2O$—); -51.7, -55.3 (2F —$OC\underline{F}_2O$—); -56.2 (3F $C\underline{F}_3OCF_2CF_2O$—); -57.8 (3F $C\underline{F}_3$—$OCF_2O$—); -87.5 (3F $C\underline{F}_3CF_2O$—); -88.4, -90.7 (4F —$OC\underline{F}_2C\underline{F}_2O$—).

The conditions used in this Example and the obtained results are summarized in Table 1.

Example 2

Syntesis in a Discontinuous Way of Monoacylfluoride $CF_3O—(CF_2CF_2O)_m(CF_2O)_n—CF_2C(O)F$ by fluorination of the corresponding diacylfluorides on CsF catalyst at the temperature of 20° C. and subsequent decomposition in situ of the obtained hypofluorites.

One proceeds as in the Example, 1, by introducing 2 mmoles of diacylfluoride (IIIA) but by feeding 2.03 mmoles of fluorine.

The reaction mixture is heated to 20° C. and maintained at this temperature for 4 hours. It is cooled to $-196°$ C. and it is noticed that the fluorine conversion is complete. The reaction mixture is let then reach the room temperture without observing any variation of the internal pressure, which indicates that the hypofluorites formed under said conditions are stable.

The subsequent decomposition reaction is carried out as in the Example 1.

The reaction products are then recovered in $C_6F_6$ and analyzed by $^{19}F$—NMR analysis. The conversion of initial —COF end groups to quantitatively give —$OCF_3$ groups is 55%; the fed fluorine yield is 98%. The GC/MS and GC analyses have shown, besides the starting unreacted compounds c), the following reaction compounds: monoacylfluoride a) and neutral perfluoropolyether b), whose formulas are reported in the Example 1. The corresponding molar percentages, determined by gaschromatography, are the following:

a) 41%, b) 37%, c) 22%, wherein the compounds a) and b) form as described in the Example 1.

The yield of the monoacylfluorides a) calculated with respect to the initial converted diacylfluorides is 53%.

The reaction products are separated by fractional distillation.

Characterization of the Products: $^{19}$F—NMR $^{19}$F—NMR spectrum in p.p.m. with respect to $CFCl_3$ (p.p.m.=0): 13.2 (1F $\underline{F}(O)CCF_2OCF_2O$—); 13.0 (1F $\underline{F}(O)CCF_2OCF_2CF_2O$—); −51.7, −55.3 (2F —$OC\underline{F}_2O$—); −56.2 (3F $C\underline{F}_3OCF_2CF_2O$—); −57.8 (3F $C\underline{F}_3OCF_2O$—); −87.5 (3F $C\underline{F}_3CF_2O$—); −88.4, −90.7 (4F —$OC\underline{F}_2C\underline{F}_2O$—).

The conditions used in this Example and the obtained results are summarized in Table 1.

Example 3

Syntesis in a Discontinuous Way of Monoacylfluoride $CF_3O$—$(CF_2CF_2O)_m(CF_2O)_n$—$CF_2C(O)F$ by Fluorination of the corresponding diacylfluorides on KF catalyst at the temperature of −10° C. and subsequent decomposition in situ of the obtained hypofluorites.

In a 10 cc metal reactor equipped with internal thermocouple are introduced 0.11 g of KF catalyst (1.89 mmoles; Aldrich® Chemical Co., titre 99%), which is activated by drying under vacuum at 150° C. for 3 hours and successively fluorinated at 400 mbar ($4 \times 10^4$ Pa) of fluorine at the temperature of 100° C. for 2 hours. By operating likewise as in Example 1, 2 mmoles of diacylfluoride (IIIA) are introduced, then after cooling in liquid nitrogen, the optional uncondensable products ($N_2$, $O_2$) stripped, 1.82 mmoles of fluorine are added and the reaction mixture is brought to −10° C. and maintained at this temperature for 5 hours. It is cooled to −196° C. and it is noticed that the fluorine conversion is complete. The reaction mixture is then let reach the room temperature without observing any variation of the internal pressure; this indicates that the hypofluorites formed under said conditions are stable.

The decomposition reaction is carried out as in the Example 1.

The reaction products are then recovered in $C_6F_6$ and analyzed by $^{19}$F-NMR analysis. The conversion of initial —COF end groups to quantitatively give —$OCF_3$ groups is 49%; the fed fluorine yield is 98%. The GC/MS and GC analyses have shown besides the unreacted starting compounds c) the following reaction compounds: monoacylfluoride a) and neutral perfluoropolyether b), whose formulas have been reported in the Example 1.

The corresponding molar percentages, determined by gaschromatography, are the following:
a) 33%, b) 35%, c) 32%, wherein the compounds a) and b) form as described in the Example 1.

The yield of the monoacylfluorides a) calculated with respect to the initial converted diacylfluorides is 49%.

The reaction products are separated by fractional distillation.

Characterization of the Products: $^{19}$F-NMR $^{19}$F-NMR spectrum in p.p.m with respect to $CFCl_3$ (p.p.m.=0): 13.2 (1F $\underline{F}(O)CCF_2OCF_2O$—); 13.0 (1F $\underline{F}(O)CCF_2OCF_2CF_2O$—); −51.7, −55.3 (2F —$OC\underline{F}_2O$—); −56.2 (3F $C\underline{F}_3OCF_2CF_2O$—); −57.8 (3F $C\underline{F}_3OCF_2O$—); −87.5 (3F $C\underline{F}_3CF_2O$—); −88.4, −90.7 (4F —$OC\underline{F}_2C\underline{F}_2O$—).

The conditions used in this Example and the obtained results are summarized in Table 1.

Example 4

Syntesis in a Discontinuous Way of Monoacylfluoride $CF_3O$—$(CF_2CF_2O)_m(CF_2O)_n$—$CF_2C(O)F$ by fluorination of the corresponding diacylfluorides on KF catalyst at the temperature of 20° C. and subsequent decomposition in situ of the obtained hypofluorites.

The used catalyst amounts and the activation are as described in the Example 3.

By operating as in the Example 1, 2 mmoles of diacylfluoride (IIIA) are introduced and 1.82 mmoles of fluorine are added.

The reaction mixture is heated to 20° C. and maintained at said temperature for 4 hours. It is cooled to −196° C. and it is noticed that the fluorine conversion is complete. The reaction mixture is let then reach the room temperture without observing any variation of the internal pressure, which indicates that the hypofluorites formed under said experimental conditions are stable.

The subsequent decomposition reaction is carried out as described in the Example 1.

The reaction products are then recovered in $C_6F_6$ and analyzed by $^{19}$F-NMR analysis. The conversion of initial —COF end groups to quantitatively give —$OCF_3$ groups is 49%; the fed fluorine yield is 98%. The GC/MS and GC analyses have shown the presence of the starting unreacted diacylfluorides c) and the formation of the following compounds: monoacylfluoride a) and neutral perfluoropolyether b), whose formulas have been reported in the Example 1. The corresponding molar percentages, determined by gaschromatography, are the following: a) 37%, b) 33%, c) 30%, wherein the compounds a) and b) form as described in the Example 1.

The yield of the monoacylfluorides a) calculated with respect to the initial converted diacylfluorides is 53%.

The reaction compounds are separated by fractional distillation.

Characterization of the Products: $^{19}$F-NMR $^{19}$F-NMR spectrum in p.p.m. with respect to $CFCl_3$ (p.p.m.=0): 13.2 (1F $\underline{F}(O)CCF_2OCF_2O$—); 13.0 (1F $\underline{F}(O)CCF_2OCF_2CF_2O$—); −51.7, −55.3 (2F —$OC\underline{F}_2O$—); −56.2 (3F $C\underline{F}_3OCF_2CF_2O$—); −57.8 (3F $C\underline{F}_3OCF_2O$—); −87.5 (3F $C\underline{F}_3CF_2O$—); −88.4, −90.7 (4F —$OC\underline{F}_2C\underline{F}_2O$—).

The conditions used in this Example and the obtained results are summarized in Table 1.

Example 5

Syntesis in a Semicontinuous Way of Monoacylfluoride $CF_3O$—$(CF_2CF_2O)_m(CF_2O)_n$—$CF_2C(O)F$ by fluorination of the corresponding diacylfluorides on CsF catalyst at the temperature of 0° C. and subsequent decomposition in situ at 40° C. of the obtained hypofluorites.

In a 260 cc metal reactor equipped with condenser, mechanical stirrer and internal thermocouple there are introduced 10 g of CsF catalyst (Aldrich®, titre 99.9%), which is dried under inert gas stream at the temperature of 200° C. for two hours and successively fluorinated with 1 Nl/h of $F_2$ diluted with 1 Nl/h of He at the temperature of 150° C. for 2 hours.

After elimination of the residual fluorine, 100 g (0.161 mmoles) of diacylfluoride (IIIA) are introduced, then the reaction mixture is brought to 0° C. by an external cryostat and the condenser temperature at the reactor top to −30° C. by means of another external cryostat. A mixture formed of 1.0 liters/h (l/h) of elemental fluorine diluted with 1.5 liters/h of helium is fluxed for 1 hour.

The IR and GC analyses of the gases outflowing from the reactor do not show any $COF_2$ formation deriving from the optional degradation of the formed hypofluorites. The reaction mixture is then very slowly heated, under temperature control by a thermostatic oil bath, up to 40° C., temperature at which it is noticed the degradation of the obtained hypofluorites with exothermal reaction with $COF_2$ formation, shown by the IR and GC analyses of the gases outflowing from the reactor.

The reaction mixture is brought to 50° C. for 1 hour to complete the hypofluoprite degradation. Once the degradation is over, the mixture temperature is brought again to 0° C. and one proceeds with a further fluorination for another hour under the previously described conditions with conversion of other diacylfluoride to hypofluorite, followed by a successive heating under temperature control up to 40° C., where it is noticed again formation of $COF_2$ deriving from the degradation of the obtained hypofluorites.

With the sequence of the described operations a total amount of fluorine of 0.091 moles is introduced.

When the reaction is over, the formed compounds, separated by filtration from the catalyst, are analyzed by $^{19}F$-NMR analysis. The conversion of initial —COF end groups to quantitatively give —$OCF_3$ groups is 30%. The fed fluorine yield is 97%.

The GC/MS and GC analyses have shown the presence of the starting unreacted diacylfluorides c) and the formation of the following compounds: monoacylfluoride a) and neutral perfluoropolyether b), whose formulas have been reported in the Example 1.

The corresponding molar percentages, determined by gaschromatography, are the following: a) 20%, b) 26%, c) 54%, wherein the compounds a) and b) form as described in the Example 1.

The yield of the monoacylfluorides a) calculated with respect to the converted diacylfluorides is 43%.
Characterization of the Products: $^{19}F$-NMR $^{19}F$-NMR spectrum in p.p.m. with respect to $CFCl_3$ (p.p.m.=0): 13.2 (1F $\underline{F}(O)CCF_2OCF_2O$—); 13.0 (1F $\underline{F}(O)CCF_2OCF_2CF_2O$—); −51.7, −55.3 (2F —$OC\underline{F}_2O$—); −56.2 (3F $C\underline{F}_3OCF_2CF_2O$—); −57.8 (3F $C\underline{F}_3OCF_2O$—); −87.5 (3F $C\underline{F}_3CF_2O$—); −88.4, −90.7 (4F —$OC\underline{F}_2C\underline{F}_2O$—).

The conditions used in this Example and the obtained results are summarized in Table 1.

Example 6 (Comparative)

Syntesis in a Discontinuous Way of Monoacylfluoride
$CF_3O$—$(CF_2CF_2O)_m(CF_2O)_n$—$CF_2C(O)F$ by fluorination of the corresponding diacylfluorides on CsF catalyst at the temperature of −10° C. and subsequent decomposition in situ at 70° C. of the obtained hypofluorites.

In a 10 cc metal reactor equipped with internal thermocouple there are introduced 1.0 g of CsF catalyst which is activated as described in the Example 1.

By operating likewise as in the Example 1, 4 mmoles of diacylfluorides (IIIA) and 3.64 mmoles of fluorine are introduced in the reactor and the reaction mixture is brought to −10° C. and maintained at this temperature for 8 hours. It is cooled to −196° C. and it is noticed that the fluorine conversion is complete. The reaction mixture is then let reach −10° C. without any variation of the internal pressure. This indicates that the hypofluorites formed under these conditions are stable.

Then the reactor containing the reaction mixture is immersed in an oil bath preheated at 70° C. and maintained at this temperature by an external thermostat. It is immediately noticed a rapid increase of the temperature and of the pressure inside the reactor due to the uncontrolled decomposition of the obtained hypofluorites. When the exothermal reaction is over, the reaction mixture is left at 70° C. for 1 hour. After having cooled the reaction mixture to −50° C., the IR and GC/Ms analyses of the gaseous phase show that $COF_2$ has formed in a notable amount and that volatile degradation products of the initial perfluoropolyether structure, such as $CF_4$, $C_2F_4$, and carbon residues are present. After removal of the volatile degradation products the raw reaction product is weighed, noticing a weight loss of about 40%.

The conditions used in this Example and the obtained results are summarized in Table 1.

Example 7

Example 1 has been repeated but performing the fluorination reaction at a temperature of −80° C. Data are reported in Table 1.

Example 8

Example 3 has been repeated but performing the fluorination reaction at a temperature of −80° C. Data are reported in Table 1.

TABLE 1

Examples 1-8. Summary of the features and obtained results. In the Table, a), b) and c) are as defined in Ex. 1. a) indicates monoacylfluoride, b) neutral perfluoropolyether, c) starting unreacted diacylfluoride.

| Ex. | way | M.W. (III) | Catal. | T (° C.) fluor. | T (° C.) decomp. | Conv. —COF —$OCF_3$/—COF(init.) mol. % | yield a) % with respect to reacted diacylfl. (a + b) mol. | $F_2$ conv. % mol. | % mol. int. final reaction mixture | | |
|---|---|---|---|---|---|---|---|---|---|---|---|
| | | | | | | | | | a) | b) | c) |
| 1 | disc. | 620 | CsF | −10 | +40 | 47 | 31 | 94 | 19 | 42 | 39 |
| 2 | disc. | 620 | CsF | +20 | +40 | 55 | 53 | 98 | 41 | 37 | 22 |
| 3 | disc. | 620 | KF | −10 | +40 | 49 | 49 | 98 | 33 | 35 | 32 |
| 4 | disc. | 620 | KF | +20 | +40 | 49 | 53 | 98 | 37 | 33 | 30 |
| 5 | semi-cont. | 620 | CsF | 0 | +40 | 30 | 43 | 97 | 20 | 26 | 54 |
| 7 | disc. | 620 | CsF | −80 | +40 | 49 | 26 | 98 | 15 | 43 | 42 |
| 8 | disc. | 620 | KF | −80 | +40 | 48 | 43 | 96 | 27 | 36 | 37 |

The invention claimed is:

1. A process for the synthesis of (per)fluorinated monofunctional carbonyl compounds having the following formula:

$$F-A-R_F—B—C(O)X_1 \quad (I)$$

wherein:
$X_1 = F, CF_3$;
A, B equal to or different from each other, are independently $C_1-C_5$ (per)fluoroalkylene groups or linear or branched $C_1-C_5$ (per)fluorooxyalkylene groups, optionally containing one or more Cl and/or H atoms;
$R_F$ is selected from the following groups:
—$ORf_1O$— wherein $Rf_1 = C_1-C_{20}$ perfluoroalkylene;
—$ORf_2$—, wherein $Rf_2$ is a perfluorooxyalkylene chain containing one or more of the following units statistically distributed along the backbone:
  $(C_3F_6O)$, selected between $(CF_2CF(CF_3)O)$ or $(CF—(CF_3)CF_2O)$;
  $(CFX_1O)$ wherein $X_1$ is F or $CF_3$;
  $(C_2F_4O)$;
  $(CF_2(CF_2)_{x'}CF_2O)$ wherein x' is an integer equal to 1 or 2;
  $(CR_4R_5CF_2CF_2O)$ wherein $R_4$ and $R_5$ are equal to or different from each other and selected between H, Cl, and wherein one fluorine atom of the perfluoromethylene unit is optionally substitued with H, Cl or (per)fluoroalkyl, having from 1 to 4 carbon atoms;
said process comprising the following steps:
A) obtainment of the mono-hypofluorite of formula:

$$FO—CFX_2-A-R_F—B—C(O)X_1 \quad (II)$$

by partial fluorination with elemental fluorine of the carbonyl groups of the following (per)fluorinated di-functional carbonyl compound of formula:

$$X_2(O)C-A-R_F—B—C(O)X_1 \quad (III)$$

wherein:
$X_1$, $R_F$, A and B have the above meanings;
$X_2$, equal to or different from $X_1$, has the same meanings as $X_1$;
in the presence of a catalyst based on metal fluorides having formula $MeF_y$, wherein:
Me is an alkaline or alkaline-earth metal or Ag; y=1 or 2;
B) thermal decomposition of the mono-hypofluorite of formula (II) to give (per)fluorinated mono-functional carbonyl compounds (I), according to the reaction:

$$FO—CFX_2-A-R_F—B—C(O)X_1(II)\text{- - -}\rightarrow F-A-R_F—B—C(O)X_1(I)+(O)CFX_2.$$

2. A process according to claim 1, wherein the A and B groups in the formulas (I)-(III) are selected from the following:
—$CF_2$—, —$CF(CF_3)$—, —$CF_2CF_2$—, —$CF_2CF_2CF_2$—, —$CF_2CF(CF_3)$—, —$CF(CF_3)CF_2$—, —$CF(OCF_3)$—, —$C(OCF_3)_2$—, —$C(CF_3)(OCF_3)$—.

3. A process according to claim 1, wherein when $R_F$=—$ORf_2$-, the perfluorooxyalkylene chain $Rf_2$ is selected from the following:
a') —$(CF_2CF_2O)_m(CF_2O)_n(CF_2CF(CF_3)O)_p(CF(CF_3)O)_q(CF_2CF_2CF_2O)_r$—
b') —$(CF_2O)_n(CF_2CF(CF_3)O)_p(CF(CF_3)O)_q$—,
c') —$(CF_2CF_2O)_m(CF_2O)_n$—,
wherein:
m is 0 to 100,
n is 0 to 100,
p is 0 to 60,
q is 0 to 60,
r is 0 to 60,
m+n+p+q+r being $\geq 0$ and the number average molecular weight of —$ORf_2$— is in the range 16 to 12,000.

4. A process according to claim 3, wherein the formula c'), when m and n are both present, m/n ranges from 0.2 to 12 and the number average molecular weight of —$ORf_2$ is within the values indicated in claim 3.

5. A process according to claim 1, wherein step A) is carried out in the presence or absence of solvents.

6. A process according to claim 1, wherein in step A) the molar ratio $F_2$/carbonyl groups of the compound (III) ranges from 0.05 to 0.90; the reaction temperature ranges from −80° C. to +30° C.

7. A process according to claim 1, wherein in step A) one operates in the absence of solvents.

8. A process according to claim 1, wherein in step A) the catalysts based on metal fluorides are selected from the following:
alkaline or alkaline-earth metal fluorides selected from the following: CsF, KF, RbF, LiF, NaF, $CaF_2$, $BaF_2$, $MgF_2$, $SrF_2$;
AgF;
said catalysts being used as such, or mixed with each other or optionally supported on porous material.

9. A process according to claim 8, wherein the preferred metal fluorides are CsF and KF.

10. A process according to claim 1, wherein the hypofluorite thermal decomposition reaction B) is carried out subsequently to the fluorination reaction of the (per)fluorinated di-functional carbonyl compound.

11. A process according to claim 1, wherein the hypofluorite decomposition temperature is in the range between the temperature $T_i$, at which the formula (II) hypofluorite begins to decompose with formation of $C(O)FX_2$ compounds as above defined, and $T_i+20°$ C.

12. A process according to claim 11, wherein the temperature at which the decomposition reaction is carried out is from 0° C. to +200° C.

13. A process according to claim 1, carried out in a discontinuous, semicontinuous and continuous way.

14. A process according to claim 1, wherein in step A) the fluorine conversion is higher than 90%.

15. A process according to claim 1, wherein the difunctional carbonyl (per)fluorinated compounds of formula (III) are selected from the following:
$X_2(O)CCFY_2$—$O(CF_2O)_n(CF_2CF(CF_3)O)_p(CF(CF_3)O)_q$-$CFY_1C(O)X_1$,
$X_2(O)CCFY_2$—$O(CF_2CF_2O)_m(CF_2O)_n$—$CFY_1C(O)X_1$,
wherein:
$X_1$, $X_2$, equal or different, are as above,
$Y_1$, $Y_2$, equal or different, have the $X_1$ meaning,
m, n, p, q are as above.

16. A process according to claim 15, wherein the formula (III) compounds are selected from the following:
F(O)CCF$_2$O(CF$_2$O)$_n$—CF$_2$C(O)F, F(O)CCF$_2$O(CF$_2$CF$_2$O)$_m$—CF$_2$C(O)F,
F(O)CCF$_2$O(CF$_2$CF$_2$O)$_m$(CF$_2$O)$_n$—CF$_2$C(O)F,
wherein m and n are as above defined.

17. A process according to claim 15, wherein the compounds of formula (III) are the following:
F(O)CCF$_2$OCF$_2$C(O)F, F(O)CCF$_2$OCF$_2$OCF$_2$C(O)F,
F(O)CCF$_2$OCF$_2$CF$_2$OCF$_2$C(O)F,
F(O)CCF$_2$OCF$_2$OCF$_2$CF$_2$OCF$_2$C(O)F, F(O)CCF$_2$OCF$_2$OCF$_2$OCF$_2$C(O)F,
F(O)CCF$_2$OCF$_2$CF$_2$OCF$_2$CF$_2$OCF$_2$C(O)F.

18. A process according to claim 3, wherein the number average molecular weight of —$ORf_2$— is 16 to 5,000.

19. A process according to claim 3, wherein the number average molecular weight of —ORf$_2$— is 60 to 3,000.

20. A process according to claim 6, wherein in step A) the molar ratio F$_2$/carbonyl groups of the compound (III) ranges from 0.1 to 0.80; the reaction temperature ranges from −80° C. to +30° C.

21. A process according to claim 11, wherein the temperature at which the decomposition reaction is carried out is from +40° C. to +150° C.

* * * * *